(12) United States Patent
Gy et al.

(10) Patent No.: US 9,604,876 B2
(45) Date of Patent: Mar. 28, 2017

(54) GLASS SHEET

(75) Inventors: René Gy, Bondy (FR); Julien Sellier, Paris (FR); Hugues Obame, Nogent sur Oise (FR)

(73) Assignee: SAINT-GOBAIN GLASS FRANCE, Courbevoie (FR)

( * ) Notice: Subject to any disclaimer, the term of this patent is extended or adjusted under 35 U.S.C. 154(b) by 0 days.

(21) Appl. No.: 13/821,931

(22) PCT Filed: Sep. 12, 2011

(86) PCT No.: PCT/FR2011/052076
§ 371 (c)(1),
(2), (4) Date: Apr. 3, 2013

(87) PCT Pub. No.: WO2012/035242
PCT Pub. Date: Mar. 22, 2012

(65) Prior Publication Data
US 2013/0183512 A1    Jul. 18, 2013

(30) Foreign Application Priority Data
Sep. 13, 2010   (FR) ...................... 10 57259

(51) Int. Cl.
C03C 21/00       (2006.01)
G01N 3/20        (2006.01)
G01N 3/42        (2006.01)

(52) U.S. Cl.
CPC ............ *C03C 21/002* (2013.01); *G01N 3/20* (2013.01); *G01N 3/42* (2013.01); *G01N 2203/0098* (2013.01); *Y10T 428/315* (2015.01)

(58) Field of Classification Search
CPC .. C03C 21/001; C03C 21/002; Y10T 428/315
(Continued)

(56) References Cited

U.S. PATENT DOCUMENTS 2,311,846 A * 2/1943 Littleton ................. C03B 27/00
                                                    428/410
3,107,196 A * 10/1963 Acloque ................. C03B 25/02
                                                    428/332
(Continued)

FOREIGN PATENT DOCUMENTS

| GB | 1 222 182 | 2/1971 |
|----|-----------|--------|
| JP | H10-072238 | 3/1998 |

(Continued)

OTHER PUBLICATIONS

International Search Report as issued for International Application No. PCT/FR2011/052076, dated Dec. 28, 2011.

*Primary Examiner* — Aaron Austin
*Assistant Examiner* — Zheren J Yang
(74) *Attorney, Agent, or Firm* — Pillsbury Winthrop Shaw Pittman LLP

(57) ABSTRACT

A glass sheet, the thickness of which is at most 2 mm, including a surface zone under compression and a central zone under tension, such that the depth at which the transition between compression and tension occurs is at least 100 micrometers, the ratio between the depth and the thickness being at least 0.1, the sheet additionally being such that the flexural stress at break in a "ring-on-tripod" test is at least 70 MPa, after Vickers indentation under a load of 60 N.

17 Claims, 3 Drawing Sheets

(58) Field of Classification Search
USPC .............................. 428/410; 65/30.13, 30.14
See application file for complete search history.

(56) References Cited

U.S. PATENT DOCUMENTS

| | | | | |
|---|---|---|---|---|
| 3,258,352 | A * | 6/1966 | Paymal | C03C 23/004 376/158 |
| 3,445,316 | A * | 5/1969 | Megles | C03C 21/00 264/2.6 |
| 3,751,238 | A * | 8/1973 | Grego | C03C 21/002 65/111 |
| 4,471,024 | A * | 9/1984 | Pargamin | C03C 21/00 174/137 B |
| 4,483,700 | A * | 11/1984 | Forker, Jr. | C03C 21/002 65/29.19 |
| 4,757,162 | A * | 7/1988 | Dumora | H01B 17/14 174/137 B |
| 5,547,409 | A * | 8/1996 | Nakamura | C03B 27/065 445/8 |
| 5,895,768 | A | 4/1999 | Speit | |
| 6,187,441 | B1 * | 2/2001 | Takeuchi | C03C 3/083 428/410 |
| 6,333,285 | B1 * | 12/2001 | Chopinet | C03C 3/085 428/410 |
| 8,312,739 | B2 * | 11/2012 | Lee | C03C 3/093 65/30.13 |
| 2008/0241603 | A1 * | 10/2008 | Isono | G11B 5/7315 428/846.9 |
| 2009/0197088 | A1 * | 8/2009 | Murata | C03C 3/083 428/410 |
| 2009/0202808 | A1 | 8/2009 | Glaesemann et al. | |
| 2010/0035038 | A1 * | 2/2010 | Barefoot et al. | 428/220 |
| 2010/0190038 | A1 * | 7/2010 | Osakabe | C03C 21/002 428/846.2 |
| 2010/0291353 | A1 * | 11/2010 | Dejneka | C03B 33/0222 428/192 |
| 2011/0014475 | A1 * | 1/2011 | Murata | C03B 17/064 428/410 |
| 2011/0281093 | A1 * | 11/2011 | Gulati | B32B 17/06 428/213 |
| 2012/0202040 | A1 * | 8/2012 | Barefoot | C03C 3/064 428/220 |
| 2013/0213091 | A1 * | 8/2013 | Ikeda | B01D 46/543 65/29.12 |

FOREIGN PATENT DOCUMENTS

| | | |
|---|---|---|
| JP | H11-328601 | 11/1999 |
| WO | WO 2005/042428 | 5/2005 |
| WO | WO 2007/032961 | 3/2007 |
| WO | WO 2009041348 A1 * | 4/2009 |

* cited by examiner

GLASS SHEET

CROSS-REFERENCE TO RELATED APPLICATIONS

This application is the U.S. National Stage of PCT/FR2011/052076, filed Sep. 12, 2011, which in turn claims priority to French Application No. 1057259 filed Sep. 13, 2010. The content of these applications are incorporated herein by reference in their entirety.

The invention relates to the field of thin glass sheets. It relates more particularly to thin glass sheets capable of withstanding violent shocks.

Thin glass sheets are frequently used as protective glass, viewing window or as screen for various electronic devices, in particular pocket or portable devices, such as for example smartphones, personal digital systems (sometimes referred to as "PDAs"), digital cameras, multimedia players, computers, etc. For reasons linked to the weight, it is also advantageous to use thin glass sheets as cover glass for solar, thermal or photovoltaic sensors.

The glass sheets used in such devices or applications are capable of being highly stressed from a mechanical point of view: repeated contacts with hard and sharp objects, impacts of projectiles, being dropped, etc.

In order to increase their shock resistance, it is known to create a surface zone under compression and a central zone under tension, via thermal tempering processes or ion exchange (which is sometimes referred to as "chemical tempering") processes. In the latter case, the surface substitution of an ion of the glass sheet (generally an alkali metal ion, such as sodium or lithium) by an ion of larger ion radius (generally an alkali metal ion, such as potassium or sodium) makes it possible to create at the surface of the glass sheet residual compressive stresses, down to a certain depth. In the whole of the text, a depth corresponds, in a transverse cross section, to a distance between a point under consideration and a surface of the glass sheet, measured along a normal to said surface. Similarly, in the entire remainder of the text, the stresses are parallel to the surface of the glass sheet, and are thickness stresses, in the sense that, with the exception of the edge regions, the average of the stresses over the entire thickness of the glass sheet is zero. The surface compressive stresses are in fact balanced by the presence of a central zone under tension. There is therefore a certain depth at which the transition between compression and tension occurs, which depth is referred to as "P" in the remainder of the text. The stress profile corresponds to the plot of the stress (whether it is compressive stress or tensile stress) along a transverse cross section as a function of the distance to one of the faces of the glass sheet, measured along a normal to said face.

The objective of the invention is to propose glass sheets capable of maintaining a high mechanical strength even after having been severely damaged, for example after having been repeatedly dropped.

For this purpose, one subject of the invention is a glass sheet, the thickness of which is at most 2 mm, having a surface zone under compression and a central zone under tension, such that the depth at which the transition between compression and tension occurs is at least 100 micrometers, the ratio between said depth and said thickness being at least 0.1, said sheet additionally being such that the flexural stress at break in a "ring-on-tripod" test is at least 70 MPa, after Vickers indentation under a load of 60 N.

Another subject of the invention is a method of selecting a glass sheet in which the ring-on-tripod flexural stress at break is measured after Vickers indentation, and the glass sheets are selected such that their stress at break is at least 70 MPa or even 90 or 100 MPa for an indentation load of 60 N, or even 70 N.

The protocol for measuring the stress at break is explained in detail further on, in the section of the present text that describes the examples according to the invention.

Figure 1A:
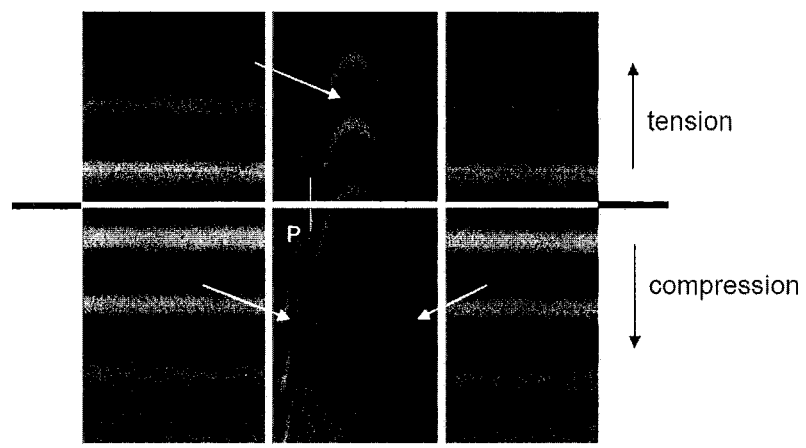
FIGS. 1a and 1b are images obtained during the observation of the edge of glass sheets.

The surface zone under compression is preferably obtained by ion exchange. More details regarding this process are given in the remainder of the present description.

The thickness e of the glass sheet is preferably at most 1.5 mm, or even 1.1 mm. The thickness of the glass sheet is preferably at least 0.25 mm. The lateral dimensions of the glass sheet depend on the targeted use. At least one dimension is generally less than or equal to 40 cm, in particular 30 cm, or even 20 cm. The surface area of the glass sheet is generally at most 0.2 $m^2$, or even 0.1 $m^2$. In applications as cover glass for solar sensors, the surface area of the glass sheet will, on the other hand, generally be at least 1 $m^2$.

The depth P at which the transition between compression and tension occurs is advantageously at least 150 micrometers, in particular 200 micrometers, or even 300 micrometers and/or at most 500 micrometers. The inventors have been able to demonstrate that large depths P make it possible to considerably increase the shock resistance of the glass sheets, which is contrary to the received idea according to which the mechanical reinforcement goes hand in hand with the intensity of the surface compressive stress. The invention thus follows a path different to that generally followed, which consists in maximizing as much as possible the surface compression, to the detriment of the depth P.

The P/e ratio between the depth P and the thickness e of the glass sheet is advantageously at least 0.15, or even 0.18.

The profile of stresses in the thickness of the glass sheet is preferably such that the maximum compressive stress is at least 70 MPa (in particular 80 MPa), the zone subjected to this maximum compressive stress being located at a non-zero distance from the surface of the glass sheet. The ratio between this distance and the thickness e of the glass sheet is preferably at least 0.01 and at most 0.1. Such a profile of stresses is particularly novel and makes it possible to achieve very large depths P and extremely high P/e ratios. Indeed, usually, the profile of stresses is such that the maximum stress is obtained at the surface of the glass sheet. With the usual profiles, which, for long exchange times, tend towards a parabolic shape, the ratio between the depth P and the thickness of the glass sheet cannot exceed the value of 0.22.

Alternatively or additionally, the profile of the stresses in the thickness of the glass sheet is preferably such that in the central zone occupying the third of the thickness of the glass, the relative variation of the intensity of the tensile stress is at least 10%, or even 15%. This novel profile in the central zone for a glass reinforced by ion exchange, which differs from the customary profile, characterized by a plateau of tensile stresses in the central zone, makes it possible to achieve higher maximum tensile stresses without however increasing the tendency to fragment in the event of breakage.

Such preferred profiles make it possible, on the other hand, to obtain a ratio between the depth P and thickness of the glass sheet preferably of at least 0.2; or even 0.25 or 0.3. The P/e ratio will generally be at most 0.4.

These preferred profiles also have lower surface compressions, commonly associated with a lower initial mechanical strength. The inventors have however been able to demonstrate that, against all expectation, the strength of the products having these stress profiles was in fact substantially improved post-damage, for example in the event of an impact. The maximum compressive stress is thus preferably less than or equal to 300 MPa, or even 200 MPa.

The profile of stresses in the thickness of the glass may be determined in a known manner using a polarizing microscope equipped with a Babinet compensator. Such a method is described by H. Aben and C. Guillemet, in "*Photoelasticity of glass*", Springer Verlag, 1993, pp. 65, 123, 124, 146.

The parameter K, defined as being the square root of the integral in the central zone under tension of the square of the stress, is preferably at most 1.4 MPa·m$^{1/2}$, or even 1.3 MPa·m$^{1/2}$. In this way, the glass sheet has the advantage of not fragmenting in the event of breaking. The term "fragmentation" is understood to mean the ability of the glass to break up forming a multitude of small fragments of glass, or even particles of glass, capable of being ejected. Even when the fragments remain in place, their small size makes the visibility through the glass sheet extremely poor or even zero. By limiting the value of the factor K, the breakage of the glass sheet is characterized, on the contrary, by the presence of a small number of cracks which, although they are not attractive, have a lesser impact on the visibility and on the propensity to eject fragments.

The "ring-on-tripod" flexural stress at break after Vickers indentation under a load of 60 N (or even 70 N) is preferably at least 80 MPa or 90 MPa and even 100 MPa.

The "ring-on-tripod" flexural stress at break after Vickers indentation under a load of 20 N is preferably at most 300 MPa, or even 200 MPa, and at least 50 MPa. Against all expectation, the choice of lower stress at break values after a lighter indentation has proved to have no effect on the post-damage strength in the event of an impact of the final product, the really distinguishing criterion being the stress at break for the heavier indentations.

The glass is preferably of the lithium or sodium aluminosilicate type. This is because this type of glass lends itself to ion exchange.

Among these glasses, a preferred glass is such that its chemical composition comprises the following oxides in the ranges of weight contents defined below:

| | |
|---|---|
| $SiO_2$ | 55-72%, in particular 60-71% |
| $Al_2O_3$ | 2-15%, in particular 3-12% |
| $Na_2O$ | 9-17%, in particular 10-15% |
| $K_2O$ | 0-12%, in particular 1-10% |
| MgO | 2-13%, in particular 4-12% |
| CaO | 0-2%, in particular 0-1% |
| $B_2O_3$ | 0-1%, in particular 0%. |

These oxides preferably represent at least 95%, or even 98% by weight of the total composition. This glass is of sodium aluminosilicate type, capable of being strengthened by an exchange of sodium ions by potassium ions.

Another preferred glass is such that its chemical composition comprises the following oxides in the ranges of weight contents defined below:

| | |
|---|---|
| $SiO_2$ | 52-75%, in particular 65-70% |
| $Al_2O_3$ | 15-27%, in particular 18-19.8% |
| $Li_2O$ | 2-10%, in particular 2.5-3.8% |
| $K_2O$ | 0-5%, in particular 0-1% |
| $Na_2O$ | 0-5%, in particular 0-1% |
| ZnO | 0-5%, in particular 1.2-2.8% |
| MgO | 0-5%, in particular 0.55-1.5% |
| BaO | 0-5%, in particular 0-1.4% |
| SrO | 0-3%, in particular 0-1.4% |
| $TiO_2$ | 0-6%, in particular 1.8-3.2% |
| $ZrO_2$ | 0-3%, in particular 1.0-2.5% |
| $P_2O_5$ | 0-8%. |

This glass is of lithium aluminosilicate type, capable of being strengthened by an exchange of lithium ions by sodium and/or potassium ions. The rate of exchange of this type of glass is particularly high, as is its scratch resistance.

The glass may also be of soda-lime-silica type, especially such that its chemical composition comprises the following oxides in the ranges of weight contents defined below:

| | |
|---|---|
| $SiO_2$ | 60-75 |
| $Al_2O_3$ | 0-4 |
| $Na_2O$ | 9-18% |
| $K_2O$ | 0-5% |
| MgO | 0-10% |
| CaO | 4-15%. |

This type of glass may also undergo ion exchanges, but the exchange times are generally very long.

Other subjects of the invention are:
an electronic device, in particular a pocket or portable device, such as, in particular, a smartphone, personal digital assistant, digital camera, multimedia player, computer, tablet, television, comprising at least one glass sheet according to the invention, as protective glass, viewing window, screen or transparent or non-transparent decorative element;
a solar, thermal or photovoltaic sensor comprising at least one glass sheet according to the invention. Another subject of the invention is a process for obtaining a glass sheet according to the invention, comprising glass melting, forming, cutting and ion exchange steps.

The forming step may be carried out by various, moreover known, processes such as the float process, in which the molten glass is poured onto a bath of molten tin, rolling between two rolls, the process referred to as the "fusion-draw" process, in which the molten glass overflows from a channel and forms a sheet via gravity, or else the process referred to as the "down-draw" process in which the molten glass flows downward through a slit, before being drawn to the desired thickness and simultaneously cooled. The cutting step is advantageously followed by a step of shaping or polishing the edges, before the ion exchange step.

The ion exchange consists in replacing some of the alkali metal ions of the glass sheet by alkali metal ions of larger ionic radius. The alkali metal ions are generally sodium or lithium, respectively partially substituted by potassium or sodium. Other ions may also be used, such as rubidium or cesium ions, or even thallium, silver or copper ions.

The ion exchange is advantageously followed by a heat treatment step (outside of the bath of molten salt), generally at the same temperature ranges as those used for the exchange. This heat treatment makes it possible to increase the P/e ratio or to decrease the intensity of the stresses. It is thus possible, in particular for lithium aluminosilicate glasses, to obtain high P/e ratios by subjecting the thin glass sheet to very short ion exchange treatments (for example for a duration of at most 2 hours or even 1 hour).

The ion exchange is generally carried out by placing the glass sheet in a bath filled with a molten salt of the desired alkali metal ion. A temperature that is high, but is below the glass transition temperature of the glass to be treated, makes it possible to initiate an interdiffusion phenomenon, impacting firstly the surface layers of the glass.

It is also possible to carry out the ion exchange by depositing a paste on the surface of the glass. The ion exchange may also be facilitated by imposing an electric field or ultrasonic waves.

At least one ion exchange step is preferably carried out using a molten potassium and/or sodium salt chosen from nitrates, sulfates, chlorides or any mixture thereof. A mixture of sodium salt and of potassium salt makes it possible to limit the intensity of the stresses. Potassium nitrate is particularly preferred.

The exchange temperature and time should be adjusted as a function of the composition of the glass, of its thickness, and of the desired profile of stresses. The inventors have been able to demonstrate that an increase in the exchange temperature and in the exchange time makes it possible to increase the depth P and to obtain the novel profile described previously, in which the zone subjected to the maximum compressive stress is located at a non-zero distance from the surface of the glass sheet, which profile, let's not forget, makes it possible to achieve particularly high P/e ratios, of at least 0.2, or even 0.25. The novel profile, in which, in the central zone occupying the third of the thickness of the glass, the relative variation of the intensity of the tensile stress is at least 10%, may itself also be obtained by an increase of the exchange temperature and of the exchange time, by the use of a thinner glass sheet or else using a subsequent heat treatment as defined previously.

In particular for sodium aluminosilicates as described previously, the exchange temperature is preferably at least 450° C., or even 480° C. The surface structural relaxation permitted by these high temperatures makes it possible to achieve the aforementioned novel profile, in particular for exchange times of at least 48 hours, or even 72 hours.

The following non-limiting examples illustrate the present invention.

The glass used for the various examples (apart from the comparative example C4) is a sodium aluminosilicate having the following weight composition.

| | |
|---|---|
| $SiO_2$ | 62% |
| $Al_2O_3$ | 8% |
| $Na_2O$ | 12.5% |
| $K_2O$ | 9% |
| MgO | 7.5% |
| CaO | 0.5%. |

Glass sheets of this composition were produced by the float process at a thickness of 3 mm, then polished in order to achieve a thickness e of around 1 mm. These glass sheets were subjected to various ion exchange treatments, carried out by immersing the glass sheet in a bath of molten potassium nitrate. The glass sheet of the comparative example C4 has a soda-lime-silica type composition and a thickness of 2 mm.

Table 1 below summarizes, for the various examples, the exchange temperature (in ° C.) and the exchange time (in hours), the depth P at which the transition between compression and tension occurs and the P/e ratio, e being the thickness of the glass sheet, and also the parameter V, which corresponds to the relative stress variation observed in the central zone occupying the third of the thickness of the glass sheet. V is calculated as the maximum stress variation in the central zone, divided by the maximum of the stress.

The stress profile, from which the values of P, V and the stress values are taken, is determined using a polarizing microscope equipped with a Babinet compensator.

TABLE 1

| Example | Temperature (° C.) | Time (hours) | P (μm) | e (mm) | P/e | V (%) |
|---|---|---|---|---|---|---|
| C1 | 360 | 32 | 31 | 0.98 | 0.03 | 3 |
| C2 | 380 | 24 | 38 | 0.96 | 0.04 | 4 |
| C3 | 380 | 34 | 46 | 0.90 | 0.05 | 4 |
| C4 | 460 | 432 | 90 | 1.95 | 0.05 | 2 |
| 1 | 490 | 24 | 125 | 0.98 | 0.13 | 7 |
| 2 | 490 | 48 | 234 | 0.97 | 0.24 | 30 |
| 3 | 490 | 72 | 270 | 1.06 | 0.25 | 36 |
| 4 | 490 | 96 | 280 | 0.98 | 0.29 | 69 |
| 5 | 490 | 120 | 309 | 0.98 | 0.32 | 69 |
| 6 | 490 | 144 | 315 | 1.05 | 0.30 | 71 |
| 7 | 490 | 168 | 320 | 0.97 | 0.32 | 108 |

Examples C1 to C4 are comparative examples.

It can be deduced from the results of table 1 that the application of high temperatures makes it possible to considerably increase the depth P. By increasing the treatment time, the P/e ratio can very widely exceed the theoretical limit of 0.2.

Table 2 below indicates, for each sample, the value of the maximum tensile stress, the value of the maximum compressive stress, the value of the parameter K and the number of fragments obtained when the glass is broken. A high number is characteristic of a fragmentation of the glass.

The fragmentation is characterized by the density of fragments after breakage. For this, test specimens are coated with an adhesive film on both faces. Then the glass is impacted at 1 cm from one of its corners, using a carbide tip and a hammer. The count of the number of fragments is carried out at at least 2 cm from the point of impact, in a 3×3 cm² square.

TABLE 2

| Example | Maximum tensile stress (MPa) | Maximum compressive stress (MPa) | K (MPa · $m^{1/2}$) | Number of fragments |
|---|---|---|---|---|
| C1 | 33 | >500 | 1.0 | 1 |
| C2 | 36 | >500 | 1.1 | 1 |
| C3 | 39 | >500 | 1.2 | 1 |
| C4 | <15 | 270 | <0.4 | 1 |
| 1 | 72 | >300 | 1.6 | 58 |
| 2 | 74 | >150 | 1.4 | 17 |
| 3 | 68 | 91 | 1.3 | 1 |
| 4 | 56 | 56 | 0.7 | 1 |
| 5 | 47 | 37 | 0.7 | 2 |
| 6 | 39 | 35 | 0.5 | 1 |
| 7 | 12 | 21 | 0.2 | 1 |

Figure 1B:
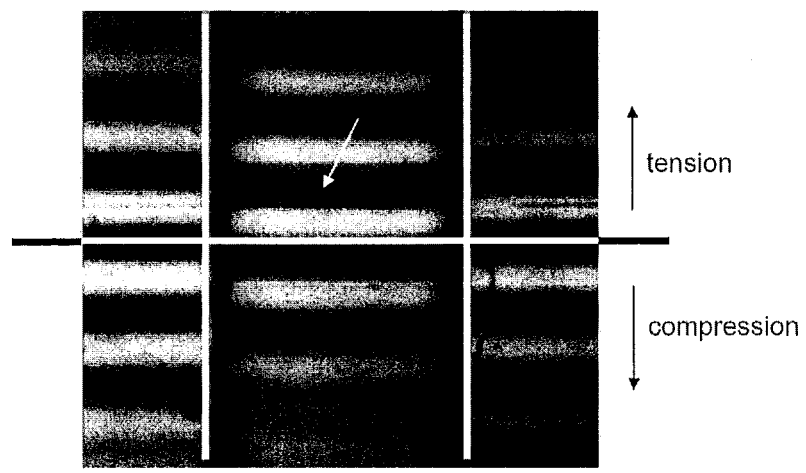

FIGS. 1a and 1b are images obtained during the observation of the edge of the glass sheets of examples 3 and C3 using a polarizing microscope equipped with a Babinet compensator. Such a device, commonly used in the art, makes it possible to determine the profile of stresses in the thickness of the glass, that is to say the value of the stress as a function of the depth. The shape of the interference fringes observed using the device reproduces the distribution of stresses at the core of the glass sheet, whereas the offsetting of the fringes is proportional to the intensity of the stress. The reference level is set arbitrarily on the darkest fringe, and the variation of this fringe (indexed on the figure by the white arrows) makes it possible to determine the stress profile. The tensile stresses correspond to the fringes located above the reference level, the compressive stresses lying underneath. The fringes become difficult to discern close to the surface if the stress gradient is too large.

The depth at which the black fringe traverses the reference level is the depth P. The profile of the glass sheet of example 3 is particularly atypical, since it has a P/e ratio of greater than 0.22, and a high relative variation of the tensile stress at the central zone, free of any plateau. On the contrary, comparative example C3 has a P/e of only 0.05, with an almost constant core tensile stress.

Figure 2:
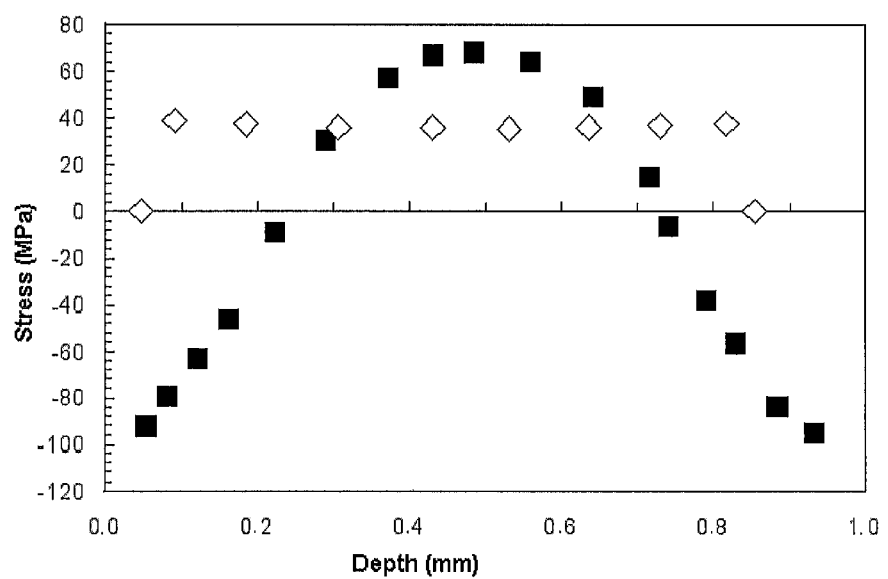
FIG. 2 shows profiles of stresses.

In FIG. 2, the profiles of stresses are plotted for example 3 (solid square points) and for comparative example C3 (open lozenge points). As is customary, the compressive stresses are negative while the tensile stresses are represented by positive values. The exact values of the compressive stress at the outer surface are not indicated because the measurement becomes difficult close to the surface if the stress gradient therein is too large.

Figure 3:
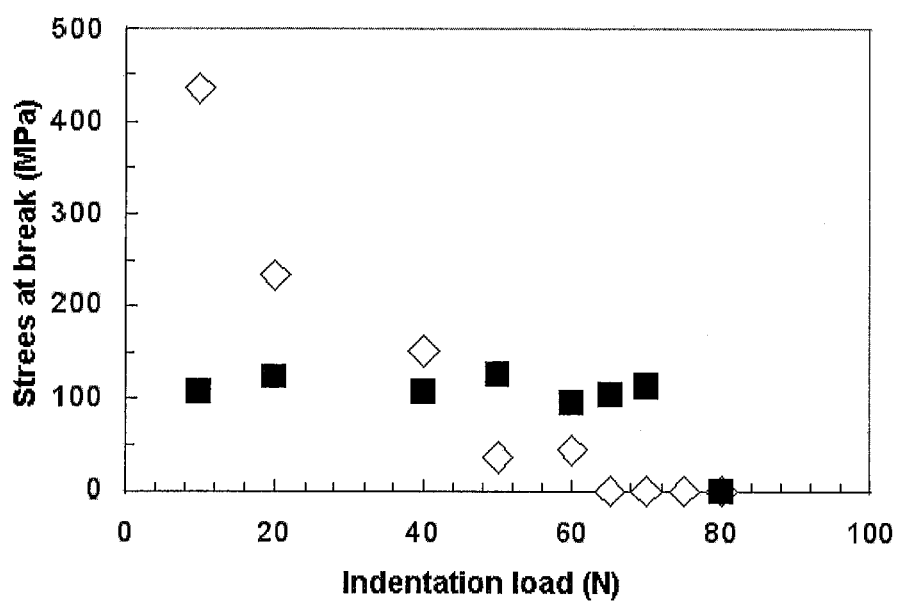
FIG. 3 shows the stress at break in the "ring-on-tripod" flexural test (expressed in MPa) as a function of the Vickers indentation load.

The results of the tests are represented in FIG. 3, which plots the stress at break in the "ring-on-tripod" flexural test (expressed in MPa) as a function of the Vickers indentation load previously experienced.

The ring-on-tripod flexural stress at break after indentation is measured in the following manner, the result being taken as the average of 5 tests. Test specimens of 70×70 mm² are cut in a glass sheet that has not undergone any treatment after its manufacture. After ion exchange, the test specimens are cleaned with water and dried.

Any one face of each test specimen is then coated with an adhesive film on a face which will be subsequently put under compression. The role of this film is to enable the location of the origin of failure.

The indentation is carried out on the face opposite the adhesive film, using weights placed on top of a Vickers tip. The test specimen is positioned under the tip so that the indentation is carried out in the middle of the test specimen, to within 1 mm.

The tip is brought down onto the test specimen by virtue of an Instron 4505 machine equipped with a 5 kN load cell. In initial position, the tip is placed between 2 and 5 mm above the test specimen. Then the tip is moved toward the glass at a speed of 10 mm/min. After contact between the tip and the glass, the force applied by the machine becomes zero and only the weights placed on the tip give rise to the indentation of the glass. The indentation lasts 20 seconds, then the tip is raised by the machine.

The glass is then stored for at least 12 h in order to stabilize the propagation of the cracks. In the event of breakage after indentation but before the flexural test, the flexural stress at break is declared to be zero.

The ring-on-tripod flexural test is carried out using an Instron 4400R machine, adjusted with a crosshead descent rate of 2 mm/min, equipped with a 10 kN load cell, a ring having a diameter of 10 mm with a torus having a radius of 1 mm, attached at the end of the Instron machine, and with the aid of a stand to which 3 balls having a radius of 5 mm are bonded, positioned at 120° over a circle having a radius of 20 mm and the center of which coincides with the center of the ring.

The test specimen is placed between these 3 balls and the ring, so that the indentation mark is aligned with the center of the ring, to within 1 mm. An increasing force is then applied to the ring until the failure of the test specimen. Only the test specimens for which the origin of failure is under the ring are counted. The stress at break as a function of the force at break and of the thickness of the test specimen is given by the following formula:

$$\sigma_{(MPa)} = \frac{0.847 \times \text{force}_{(N)}}{\text{thickness}^2_{(mm)}}$$

The open lozenges are the points measured in the case of comparative example C3, while the solid squares correspond to example 3 according to the invention.

It can be seen that, owing to the higher surface compressions, the comparative example C3 has much higher stresses at break in the case of small indentations. On the other hand, this stress at break drops vertiginously when the indentation load increases, until becoming zero for loads of greater than 60 N. The glass sheet according to the invention (example 3) has a very different behavior, with a constant stress at break, of the order of 100 MPa, including for the high indentation loads, above 60 N.

Against all expectation, the much lower stress at break for the lighter indentations has not proved detrimental to the final impact resistance properties. It is on the contrary the particular choice of stress at break for the heavier indentations which may make the difference.

The invention claimed is:

1. A glass sheet, the thickness of which is at most 2 mm, comprising:
   a surface zone under compression and a central zone under tension,
      wherein the surface zone under compression has been obtained by ion exchange, such that a depth at which the transition between compression and tension occurs is at least 100 micrometers, a ratio between said depth and said thickness being at least 0.1,
   wherein said sheet additionally being such that a flexural stress at break in a "ring-on-tripod" test is at least 70 MPa, after Vickers indentation under a load of 60 N,
   wherein the maximum compressive stress in the surface zone under compression is between 21 MPa and 37 MPa,
   wherein the stress profile of the glass sheet has a parabolic shape,
   and wherein the glass is of sodium aluminosilicate type or of soda-lime-silica type glass,
      wherein the chemical composition of the sodium aluminosilicate type glass comprises the following oxides in the ranges of weight contents defined below:

| | |
|---|---|
| $SiO_2$ | 55-72%, |
| $Al_2O_3$ | 2-15%, |
| $Na_2O$ | 9-17%, |
| $K_2O$ | 0-12%, |
| MgO | 2-13%, |
| CaO | 0-2%, |
| $B_2O_3$ | 0-1%, | wherein the chemical composition of the soda-lime-silica type glass comprises the following oxides in the ranges of weight contents defined below:

| | |
|---|---|
| SiO$_2$ | 60-75 |
| Al$_2$O$_3$ | 0-4 |
| Na$_2$O | 9-18% |
| K$_2$O | 0-5% |
| MgO | 0-10% |
| CaO | 4-15%. |

2. The glass sheet as claimed in claim 1, the thickness of which is at most 1.1 mm and at least 0.25 mm.

3. The glass sheet as claimed in claim 1, wherein the depth at which the transition between compression and tension occurs is at least 200 micrometers and at most 500 micrometers.

4. The glass sheet as claimed in claim 1, wherein the ratio between the depth and the thickness is at least 0.2.

5. The glass sheet as claimed in claim 1, wherein the ratio between the depth at which the transition between compression and tension occurs and the thickness is at most 0.4.

6. The glass sheet as claimed in claim 1, wherein the parameter K is at most 1.4 MPa·m$^{1/2}$, K being the square root of the integral in the central zone under tension of the square of the stress.

7. The glass sheet as claimed in claim 6, wherein the parameter K is at most 1.3 MPa·m$^{1/2}$.

8. The glass sheet of claim 1, wherein the thickness is between 0.25 and 1.5 mm.

9. The glass sheet as claimed in claim 1 wherein said oxides comprise at least 95% by weight of the composition.

10. The glass sheet as claimed in claim 1 wherein said oxides comprise at least 98% by weight of the composition.

11. The glass sheet as claimed in claim 1, wherein said glass sheet is used in an electronic device and said electronic device is a pocket or portable device.

12. The glass sheet as claimed in claim 11, wherein the pocket or portable device is a smartphone, a personal digital assistant, a digital camera, a multimedia player, a computer, a tablet, or a television.

13. An electronic device comprising at least one glass sheet as claimed in claim 1, as protective glass, viewing window, screen or decorative element.

14. A solar, thermal or photovoltaic sensor, comprising at least one glass sheet as claimed in claim 1.

15. A process for obtaining a glass sheet as claimed in claim 1, comprising glass melting, forming, cutting and ion exchange steps.

16. The process as claimed in claim 15, comprising carrying out at least one ion exchange using a molten potassium and/or sodium salt chosen from nitrates, sulfates, chlorides or any mixture thereof.

17. The process as claimed in claim 15, wherein an exchange temperature is at least 450° C.

* * * * *